(12) United States Patent
Chiu et al.

(10) Patent No.: US 6,551,338 B1
(45) Date of Patent: Apr. 22, 2003

(54) METHOD AND DEVICE FOR MYOGENESIS AND ANGIOGENESIS OF THE HEART

(75) Inventors: Ray Chu-Jeng Chiu, Montreal (CA); Kevin Lachapelle, Westmount (CA)

(73) Assignee: McGill University, Montreal (CA)

( * ) Notice: Subject to any disclaimer, the term of this patent is extended or adjusted under 35 U.S.C. 154(b) by 221 days.

(21) Appl. No.: 09/651,268

(22) Filed: Aug. 30, 2000

Related U.S. Application Data
(60) Provisional application No. 60/151,922, filed on Sep. 1, 1999.

(51) Int. Cl.[7] ............................................. A61B 17/34
(52) U.S. Cl. ........................ 606/186; 606/185; 128/898
(58) Field of Search ................................ 606/167, 185, 606/186, 181, 184, 170; 128/898

(56) References Cited

U.S. PATENT DOCUMENTS

| | | | |
|---|---|---|---|
| 699,915 A | * 5/1902 | Foultz | 101/30 |
| 1,515,050 A | * 11/1924 | Jensen | 101/20 |
| 5,250,067 A | * 10/1993 | Gelfer et al. | 606/185 |
| 5,938,632 A | 8/1999 | Ellis | |
| 6,030,404 A | * 2/2000 | Lawson et al. | 606/186 |
| 6,045,565 A | 4/2000 | Ellis et al. | |
| 6,063,082 A | 5/2000 | DeVore et al. | |
| 6,093,185 A | 7/2000 | Ellis et al. | |
| 6,143,019 A | * 11/2000 | Motamedi et al. | 128/898 |

OTHER PUBLICATIONS

Angiogenesis and Growth Factor Expression in a Model of Transmyocardial Revascularization—Pelletier et al, 1998 by The Society of Thoracic Surgeons, published by Elsevier Science Inc.(Ann. Thorac. Surg. 1998;66:12–8).

Angiogenesis in Transmyocardial Revascularization: Comparison of Laser Versus Mechanical Punctures—Chu et al, 1999 by The Society of Thoracic Surgeons, published by Elsevier Science Inc. (Ann Thorac Surg 1999;68:301–8).

Angiogenic Response Induced by mechanical Transmyocardial Revascularization, Chu et al, The Journal of Thoracic and Cardiovascular Surgery, 1999.

* cited by examiner

*Primary Examiner*—Danny Worrell
(74) *Attorney, Agent, or Firm*—Ogilvy Renault

(57) ABSTRACT

Revascularization of an ischemic myocardium is achieved through the stimulation of angiogenesis (new blood vessel formation) by causing an injury to the heart via puncturing and traversing the ischemic myocardium from the epicardium to the endocardium simultaneously, at a plurality of spaced apart sites, with a plurality of needles, and simultaneously withdrawing the plurality of needles from the punctured ischemic myocardium; the technique and the device have advantages over the use of lasers for this purpose an additional advantage is that the revascularization can be performed without open chest surgery or conventional sternotomy although it can also be employed in conjunction with these surgical procedures; thus, by way of example, the revascularization can be performed transthoracically; with a t sternotomy, a thoracotomy incision or thoracoscopically; the puncturing operation may also be employed in myogenesis of a myocardium by delivery of desired agents to the myocardium through the puncturing needles; such myogenesis may be carried out simultaneously with revascularization of an ischemic or failing myocardium or as an independent operation.

18 Claims, 3 Drawing Sheets

METHOD AND DEVICE FOR MYOGENESIS AND ANGIOGENESIS OF THE HEART

CROSS-REFERENCE TO RELATED APPLICATION

This Application is related to U.S. Application No. 60/151,922, filed Sep. 1, 1999, and the benefit under 35 U.S.C. 119(e) of such U.S. Application is claimed.

BACKGROUND OF THE INVENTION i) Field of the Invention

The invention relates to a method of myogenesis and/or angiogenesis in a heart, including revascularization an ischemic myocardium, and to a device for myogenesis and/or angiogenesis, including revascularizing of an ischemic myocardium.

ii) Description of Prior Art

Transmyocardial laser revascularization (TMLR) has been employed in clinical trials to reduce angina. This laser technology was developed in the belief that channels formed in the myocardium by the laser would provide a replacement vascular system.

It has now been found that the laser channels do not remain intact; although increased vascular density is maintained. It has now been found that contrary to the original hypothesis of a laser channel serving as a conduit for new blood flow from the ventricular cavity to the myocardium, the physiological basis of TMLR appears to be angiogenesis caused by non-specific tissue damage.

The laser technology has the disadvantage that it is costly, the equipment currently (1999) having a cost of the order of $250,000 to 350,000 (U.S.), and requires sophisticated monitoring for its safe use.

Angiogenesis is employed to treat an ischemic myocardium employing angiogenesis provoking agents.

Myogenesis is employed to treat a failing myocardium such as by administration of growth factors.

SUMMARY OF THE INVENTION

It is an object of the invention to provide a new method of revascularization on ischemic myocardium.

It is another object of the invention to provide a new device for revascularizing an ischemic myocardium.

A further object of the invention is to provide a method of myogenesis and/or angiogenesis in a failing heart.

A still further object of the invention is to provide a device for myogenesis and/or angiogenesis in a heart.

In accordance with one aspect of the invention, there is provided a transthoracic method of angiogenesis or myogenesis of a myocardium comprising: puncturing a myocardium, from epicardium to endocardium, simultaneously, at a plurality of spaced apart sites, with a plurality of needles, and simultaneously withdrawing the plurality of needles from the punctured myocardium.

In accordance with another aspect of the invention there is provided a device for transthoracic angiogenesis or myogenesis of a myocardium comprising: a support member dimensioned for insertion into proximity with a myocardium, a plurality of needles supported by said support member in spaced apart relationship, said needles being effective to puncture a myocardium from epicardium to endocardium.

The invention has particular application in angiogenesis for the revascularization of an ischemic myocardium, but also has application in myogenesis in the treatment of a failing heart.

In accordance with the invention it has been determined that a tissue injury-induced angiogenesis is provided in an ischemic myocardium employing needle puncture instead of laser technology.

DETAILED DESCRIPTION OF PREFERRED EMBODIMENTS OF THE INVENTION

The device of the invention has a plurality of needles which are supported, in spaced apart relationship, by a support member.

Suitably the needles extend from a face of the support member which typically will be a flat face, but might have other contours, such as a concavely curved face. Typically the needles will be in generally parallel relationship and conveniently will extend perpendicularly of a flat support face. Conveniently the device has 5 to 15, preferably about 10 needles, extending in parallel relationship from the support face.

The needles are suitably spaced apart such that adjacent needles are spaced with their central axes, 2 to 4 mm apart.

Each needle should have a length permitting a puncture in the myocardium extending from the epicardium to the endocardium. This puncture depth will vary in individual patients but generally the puncture depth will be 6 to 20 mm, more usually 8 to 15 mm. The needles have a length necessary to meet the desired depth of penetration. In use the surgeon will typically have access to a plurality of devices of the invention, which may differ in the lengths of the needles, so that a particular length can be selected based on the patient and the desired depth of penetration.

The needle should have a maximum diameter of at least 1.25 mm and generally 1.25 to 1.8 mm to provide a puncture of adequate transverse dimension to provide a wound for the purpose of the invention. The wound or injury to the myocardium caused by the punctures with the needles in the device of the invention causes an increase in perfusion.

The reference to "maximum" diameter here in contemplates the diameter of the body of the needle as distinct from the point and adjacent portions, since the body will taper to the point, in a short region adjacent the point. Furthermore the reference to "diameter" is not intended to be construed as limiting the needles to being of circular cross-section, and "diameter" in reference to the needles is to be understood as identifying the major cross-sectional dimension of the needles. Preferably, however, the needles will have a circular or substantially circular cross-section.

It will be understood that a single device of the invention may be employed to provide more than one cluster of punctures, such as by puncturing adjacent zones of the myocardium with the same device to provide a desired area of punctures.

By selecting a device of the invention of appropriate physical parameters with respect to needle dimensions, and number of needles, the surgeon can control both the puncture density and depth as required based on the needs of individual patients. Furthermore the employment of the simultaneous puncturing of the invention, shortens and simplifies the surgical procedure, with the consequent benefit to the patient.

Depending on the mode of use or route of deployment the needles may be fully exposed at all time, for example, in a conventional sternotomy; or the needles may be temporarily shielded prior to and following the puncturing to avoid damage to adjacent members during the introduction of the device to the region of the myocardium. Thus, if employed in key hole surgery, the device is fed through a port into the chest cavity and the needles are temporarily shielded during the feeding.

In a particular embodiment in which the needles are to be temporarily shielded, there is additionally included a shield, the shield and support member being integrally connected and at least one of the shield and support member is movable relative to the other from a first position in which the needles are concealed, in a non-puncturing configuration, by the shield, to a second position in which the needles are exposed for puncturing. In the first position in which the needles are in the non-puncturing configuration the support member can be readily inserted into the chest cavity such as by minimally invasive thoracotomy, without danger of the needles inadvertently injuring tissue during the insertion into the chest cavity.

In use the support member, with the needles concealed, is brought into close proximity with the heart, for example, an ischemic myocardium, and the needles are exposed to puncture the heart, for example, the ischemic myocardium by adjusting the support member to the second position. In one embodiment a shield face of the shield has orifices therethrough aligned with the needles, and the support member and needles are displaceable relative to the shield face so that the needles extend through the orifice to the exposed second position.

On completion of the required puncturing of the ischemic myocardium, the needles are withdrawn to the concealed configuration such as by displacing the support member relative to the shield face of the shield so that the needles are retracted through the orifices, and the device can be withdrawn from the chest cavity.

In a further preferred embodiment conduits extend through all or some of the needles, each conduit having an inlet and an outlet. Each inlet communicates with a hollow supply zone in the interior of the support member, for supply of an agent such as an exogeneous angiogenic factor or drug; each outlet is at the needle point. In this way a desired angiogenic factor or factors can be injected at the puncture sites of the ischemic myocardium. It is found that such factors enhance the revascularization.

Suitable angiogenic factors include VEGF (vascular endothelial growth factor).

The device can also be employed to deliver other agents at the puncture sites for myogenesis or angiogenesis, including implanting of myoblasts or stem cells to grow new muscles, and cardiomyocyte precursor cells.

A particular advantage of the invention is that the device can be employed with minimally invasive surgery; but the method employing the device, can also be carried out with open chest surgery or conventional sternotomy.

Minimally invasive techniques which can be employed include introducing the device transthoracically or. The device could also be introduced through a left thoracotomy incision which is an opening between the ribs of the patient, or it could be done thoracoscopically through the use of three small incisions where the device would be introduced into the chest cavity.

In the sternotomy approach the device could be applied to the heart in conjunction with conventional coronary artery bypass surgery. The device used at this stage would not necessarily need any protective shield as it is being used directly onto the heart with complete exposure and safety. The device could be similar to that as is described below in FIGS. 1A–1C. In addition, a similar type of device could be used through the thoracotomy which again gives direct and open access to the ischemic myocardium. In using the device through a thoracoscope which is the use of three small incisions on the left side of the chest cavity, the device would be such that it slides within a shield as described below, positioned appropriately to the area of the ischemic myocardium, allowed to open much like an umbrella and then pierce the myocardium. This device could be withdrawn within the protective covering of the shield and then withdrawn completely outside of the chest.

The device might also be introduced by percutaneous access through the femoral artery, in this case the device is passed up through the femoral artery into the aorta down through the aortic valve and into the left ventricle cavity as is done during cardiac catheterization. A protective sleeve follows the device into the left ventricular cavity and the device is then pushed out through the sleeve, opens up like an umbrella and is allowed to press up against the left ventricular cavity creating the punctures using the needles. The needles are removed by bringing them back into the protective sheath and then withdrawing the sheath and device completely out of the femoral artery. Entry to the femoral artery may be through standard femoral artery sheaths which are used during cardiac catheterization.

On the other hand there are disadvantages in such percutaneous access, and the present invention overcomes such disadvantages. In particular, coronary arteries are at the surface of the heart (epicardial) and thus when external punctures are formed as in the transthoracic method of the invention, the surgeon is able to view the coronary arteries, and avoid puncturing them. Employing percutaneous access, on the other hand, results in the punctures being formed from internally of the heart, towards the exterior; in this approach the coronary arteries cannot be seen by the surgeon. If the coronary arteries are inadvertently punctured from the interior of the heart, massive myocardial infarctions i.e. heart attack may occur which can result in immediate death of the patient. In addition traversing the entire myocardium from the endocardium to the epicardium might result in external bleeding around the heart and cause cardiac compression. The use of percutaneous access thus necessitates employment of complex equipment to determine at all times the relative locations of the needles and the coronary arteries, so as to minimize the potential for inadvertently puncturing the coronary arteries.

If used in key hole surgery the device slides through a port into the chest cavity with needles protected by a shield or sleeve as outlined hereinbefore. When the position of the heart is determined, the needles are exposed such as by adjustment of their position relative to the shield member. Suitably the support member for the needles may have a flexible hinge at its centre such that the support member can move at a 90° angle in one geometric plane. In this way the support member may be concealed within the protective shield during passage in and out of the chest cavity. At the site of employment the needles are exposed and the support member flexes 90° such that the needles point directly at the heart. Suitably the device will have a spring handle permitting for control of depth or puncture penetration.

The use of hollow needles allows for delivery of agents, for example, angiogenic and myogenic factors.

Finally the device can be introduced through a conventional sternotomy which involves cutting open the breast bone as is done in usual coronary artery surgery.

DESCRIPTION WITH REFERENCE TO DRAWINGS

Figure 1:
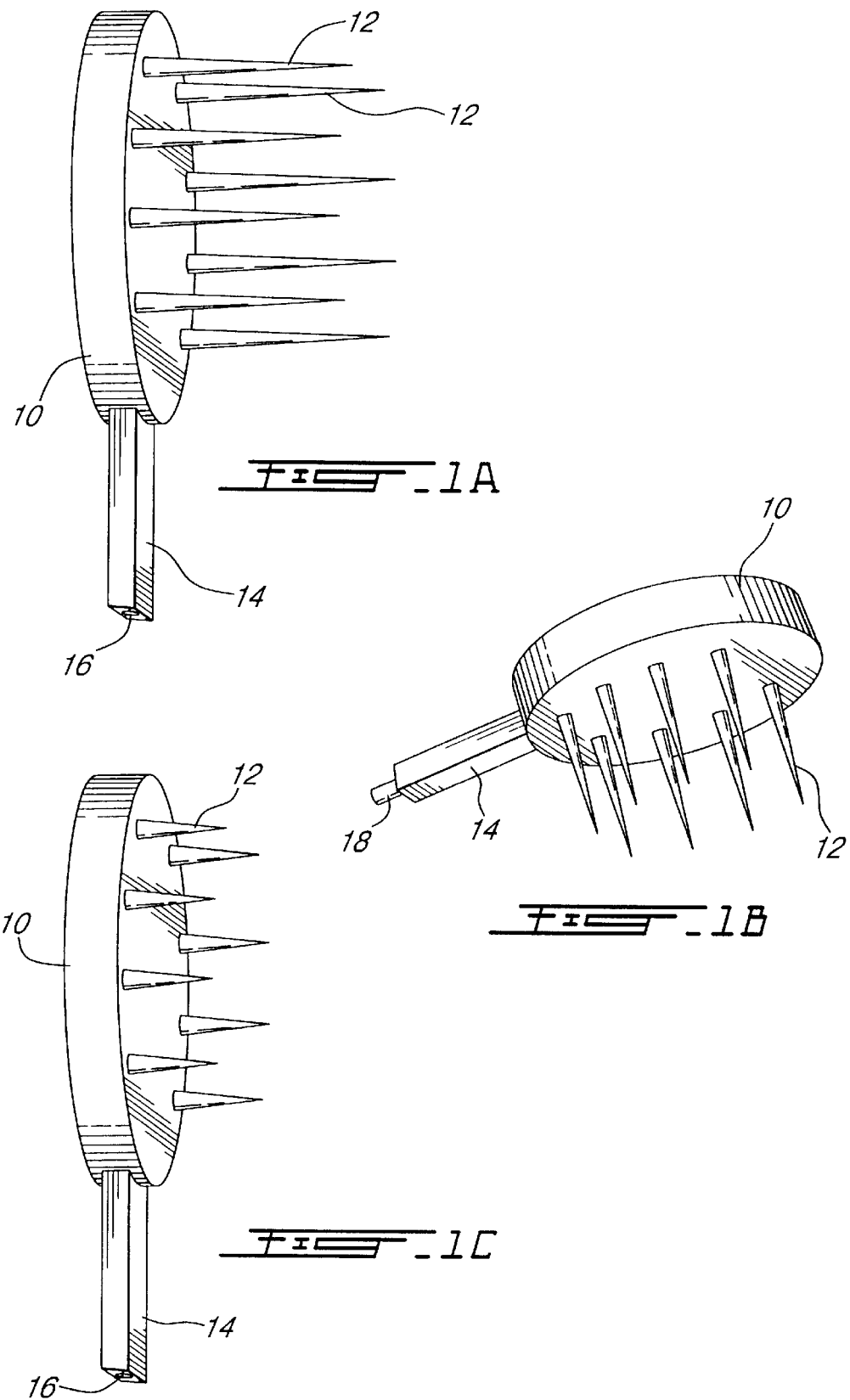
FIGS. 1A, 1B and 1C show different embodiments of a support member of the device of the invention, having puncturing needles mounted thereon.

With particular reference to FIGS. 1A, 1B and 1C, a support member 10 of a device of the invention supports a plurality of spaced apart needles 12, the support member 10 has a detachable malleable handle 14 and the needles 12 may be of different lengths to allow for different depth of penetration into the myocardium.

Different support members 10 may be of different size and have different numbers of needles 12 in different spaced relationships depending on the clinical situation.

In a particular embodiment the needles 12 are hollow and communicate via a supply zone in the interior of support member 10, with a hollow passage 16 in handle 14, which passage communicates with a conduit 18 (see FIG. 1B) for controlled delivery of agents into the myocardium via the needles 12.

Figure 2:
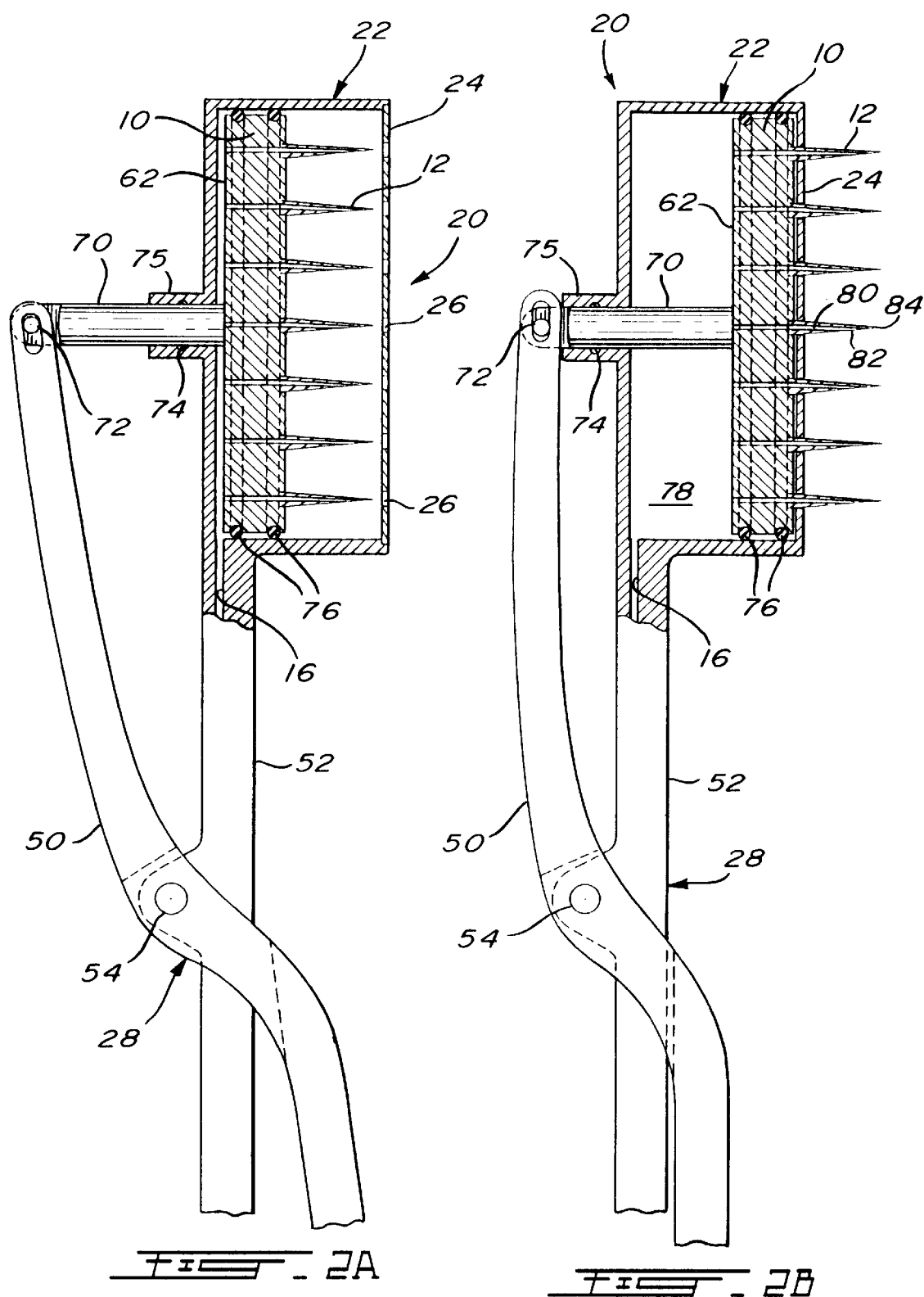
FIGS. 2A and 2B are schematic representations of a device of the invention with the needles in concealed non-puncturing configuration, and exposed puncturing configuration, respectively.

With further reference to FIGS. 2A and 2B, a device 20 of the invention is partially illustrated. Device 20 has a shield 22 which houses support member 10 having needles 12 as described in FIGS. 1A, 1B and 1C on front side 60. Shield 22 has a shield face 24 having a plurality of orifices 26, each orifice 26 being aligned with a needle 12.

A scissor mechanism 28 having legs 50 and 52 pivoted about a pivot 54 interconnects support member 10 and shield 22 for movement of support member 10 with needles 12, relative to shield face 24 between the concealed non-puncturing configuration of FIG. 2A and the puncturing configuration illustrated in FIG. 2B.

Leg 50 is a goose neck leg having an arm 70. Leg 50 is pivoted at pivot 72 centrally of a rear side 62 of support member 10 and is connected to rear side 62 by arm 70. A seal 74 extends about arm 70 between arm 70 and port 75 of shield 22. A seal 76 extends peripherally of support member 10, between support member 10 and shield 22.

Leg 52 has an inner passage 16 for flow of an agent to be administered, if desired. The passage 16 communicates with the interspace 78 between shield 22 and rear side 62 of support member 10.

The needles 12, or at least some of needles 12, have passages or conduits 80 therethrough, terminating at outlets 82 at the needle points 84.

A desired agent is introduced into interspace 78 under pressure, during puncturing with needles 12, and flows under pressure through conduits 80 and enters the puncture sites, of the myocardium at outlets 82.

Figure 3:
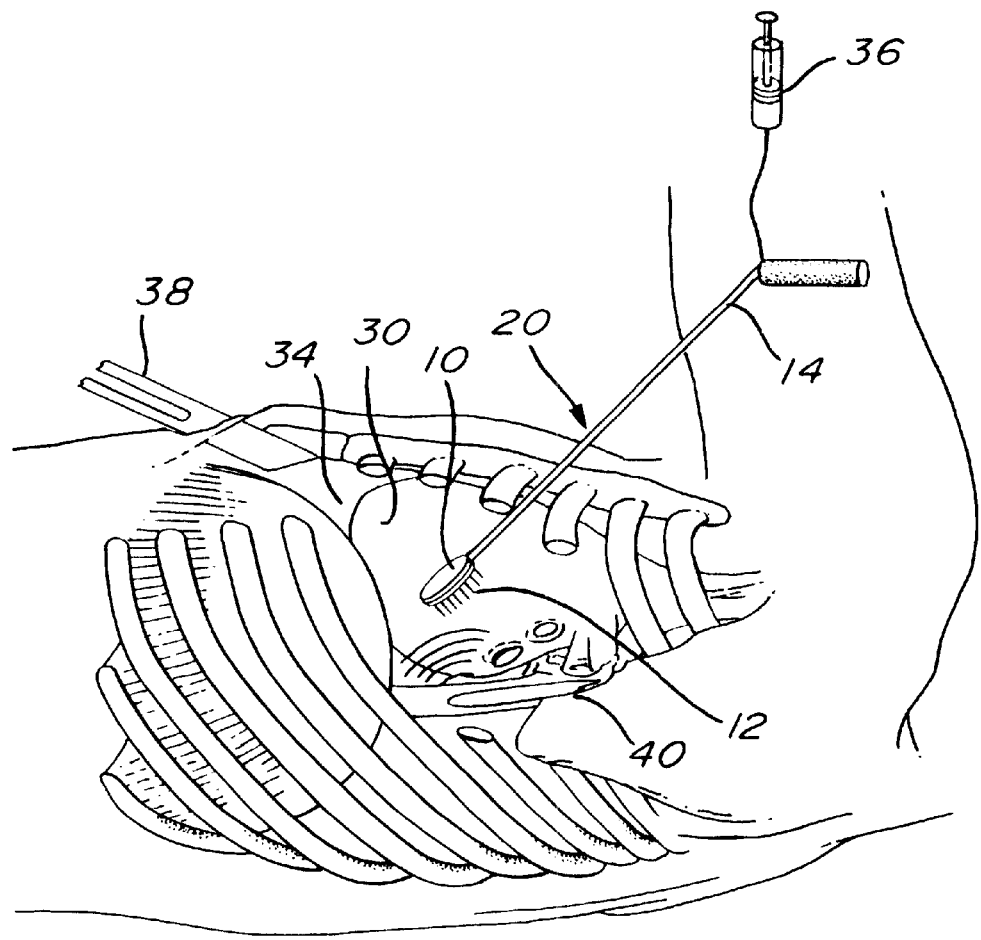
FIG. 3 illustrates schematically a revascularization employing the device of the invention.

With further reference to FIG. 3, the method of the invention is illustrated. A device 20 of the invention is applied to a heart 30 to revascularize an ischemic myocardium of the heart 30 in chest cavity 34. In the embodiment in which the device 20 employs the support member 10 having hollow needles 12, a needle 36 injects an agent for example growth factors or genes to the needles 12.

A thoracoscopy 38 permits visualization of the heart during the method; and a transesophageal echocardiogram 40 permits determination of the depth of needle penetration.

In preferred embodiments and methods, as described, the support member 10 has the form of a disc with multiple needles 12 at one end of malleable handle 14.

The device, as illustrated in FIGS. 1A, 1B and 1C, is composed of a disc with multiple needles at the tip of a malleable handle. The handle 16 and a number of needles 12 on the disc may be hollow, (as illustrated in FIGS. 2A and 2B) allowing injection of medications such as angiogenic factors using a syringe which can be attached to the opposite end of the handle 14 (as shown in FIG. 3). The disc can be screwed onto the handle 14 and may be replaced. Several sizes of discs typically ranging from 1 to 4 cm in diameter may be employed with different density of needles per square cm of the disc surface.

The disc with sharp needles is shielded while introduced into the chest, and positioned over the site over the heart to avoid inadvertent tissue injury by the sharp needles 12. A triggering mechanism exposes the needles 12 to penetrate the myocardium. Then the needles 12 will be withdrawn within the shield 22 for removal of the device 20 from the patient (see FIGS. 2A and 2B).

Typically a support member 10 may have 10 to 30 needles 12, each needle being a 20 gauge needle of about 1–2 cm length. In general there will be a set of such support member 10 with various numbers and sizes of needles, so that an appropriate choice can be made for the individual patient and situation.

In the case in which the device is to be introduced to the ischemic myocardium by a minimally invasive technique, the device is dimensional for insertion into proximity with an ischemic myocardium by such minimally invasive technique which typically will be of a type described herein.

Description of Surgical Technique to Use the Device

Under general anesthesia, patients are properly positioned depending on the area of the myocardium to be revascularized. For example, for the anterolateral aspect of the left ventricle, a supine or lateral position may be chosen; whereas for the posterior aspect, a deep Trendelenberg position may be used. Through a small incision in the left anterior chest wall, a video camera scope is introduced and the heart inspected. Another small incision made near the apex of the heart allows the introduction of VATS equipment to open the pericardium longitudinally anterior to the left phrenic nerve. Based on the inspection of the heart through the scope, the surgeon chooses the appropriate needle disc to be attached to the handle, and the malleable handle is manually bent to the desired curvature and angle to reach the desired portion of the heart. Again, under video scopic guidance the device is inserted through the lower incision, while the needles are protected to avoid getting caught in the chest wall. Once in the epicardial area, a trigger exposes the needles, and the disc firmly compressed against the surface of the heart will create the desired needle punctures at the ischemic myocardium. If the surgeon so chooses, appropriate angiogenic factors or other medications can be injected through the opposite end of the handle while the disc is pressed against the heart. The disc is then moved away from the heart perpendicularly to avoid myocardial tear, placed within the shield, withdrawn and removed from the chest. Inspection will be made to assure hemostasis. If necessary, Surgicel™ may be placed over the epicardium and pressure maintained using VATS instruments. Following this, the chest will be drained with a small chest tube, and the two small incisions closed in the routine manner.

Other techniques may be employed as follows:
a) Sternotomy Approach

The patient is under general anesthesia. In a supine position the sternotomy is performed in the usual fashion.

The pericardium is liberated from the heart and suspended. At this time the patient may or may not undergo conventional aorto-coronary bypass surgery. The area of the heart that needs to be revascularized is located. The heart is stabilized using manual traction, the hand held device is then used to puncture the myocardium. A trigger exposes the needles and the disc is firmly compressed against the surface of the heart and creates the desired needle punctures in this area of ischemic myocardium. If the surgeon so chooses appropriate antiogenic factors can be injected through the handle while the disc is pressed against the heart. The disc is then removed from the heart and withdrawn from the chest. Any bleeding from the epicardium can be controlled with Surgicel™ and/or pressure.

b) Thoracotomy Approach

Under general anesthesia, the patient is placed in the right lateral decubitus position and a standard antero-lateral thoracotomy is performed. The myocardium is approached through the fourth or fifth interspace depending on the surgeon's preference. The ribs are retracted using standard thoracotomy instruments. The rest of the procedure is similar to the technique used during the sternotomy.

c) Percutaneous Approach through the Femoral Artery

As indicated above the percutaneous approach has disadvantages which the transthoracic method of the invention overcomes. A percutaneous approach is generally done in the Cardiac Catheterization Laboratory and performed by a surgeon or a cardiologist. Access into the femoral artery is performed using the standard Seldinger technique in which a femoral artery sheath of various sizes is inserted in over a previously placed guide wire. The guide wire is then placed up through the femoral artery into the aorta passed the aortic valve and into the ventricular cavity under fluoroscopic guidance. Once in the ventricular cavity, the device along with its protective sheath glides over the guide wire through the femoral artery sheath into the femoral artery up the aorta across the aortic valve and into the ventricular cavity. The guide wire is then removed. Under fluoroscopic guidance the device itself is pushed out of its protective sheath and a trigger opens the umbrella which is composed of numerous needles. The device is then firmly compressed against the interior surface of the heart and creates the desired needle punctures at the ischemic myocardium. Once terminated, the needles are withdrawn within the protective sheath much like the closing of an umbrella. The sheaths of the device are then removed completely by withdrawing out of the femoral artery sheath. The femoral artery sheaths could then be removed according to the standard catheterization protocols.

General Purpose and Commercial Applications

The patient population benefiting from this operation are those with severe anginal pain, and those for whom anatomical reasons or due to numerous previous bypass operations, there is no possibility of performing conventional coronary artery balloon dilatation or bypass surgery. One example of such patient population is transplantation coronary angiopathy in patients who are undergoing chronic rejection after heart transplantation. In essence, the patient population would be identical to those who have been subjected to laser TMR.

Advantages and Improvements Over Existing Technology

The alternate technique of using a laser to make multiple cardiac punctures requires equipment in the order of ¼ to ⅓ million dollars U.S. The simple device of the invention could be manufactured and marketed at a lower cost, probably not more than $1,500.00 U.S. Safety features compared to laser equipment include, depending on the type of laser equipment it is compared to, avoidance of air embolism, and injury to the intracardiac structures. Since the device is not an implantable device and is simply used to create multiple punctures and to inject growth factors, and since the TMR process per se has been approved by the FDA, one can expect rapid approval of this device by the regulatory agencies for commercial use.

Thus, the new device achieves the following:

1) It can be used with a minimally invasive technique (video-assisted thoracotomy), avoiding an open chest procedure required for the use of lasers or ordinary needles.

2) Multiple needle punctures of ischemic myocardium can be made instantaneously and simultaneously, rather than the time consuming use of a single needle for punctures one at a time.

3) The addition of exogeneous angiogenic factors such as VEGF (vascular endothelial growth factor) which further facilitate the growth of new vessels. The device allows simultaneous injection of such growth factors at the time of puncture, which saves time as well as eliminating the need for additional surgical maneuvers.

EXAMPLE 1

Animal Model with Chronic Ischemia

Fifteen Yorkshire pigs weighing 15 to 20 kg were premedicated with intramuscular ketamine (15 mg/kg) and were anesthetized with intravenous injection of thiopental sodium (15 mg/kg). After oral endotrachial intubation, anesthesia was maintained with 0.5 to 2.0% isoflurane in room air. Oxygen saturation was continuously monitored using transcutaneous oxymeter probe. Five hundred milligrams of cefazolin was given intravenously prior to skin incision.

Animals were placed in right lateral decubitus position. The thorax area was prepared and draped in a sterile fashion. Exposure of the proximal left circumflex artery (LCx) was achieved via a mini thoracotomy through the $4^{th}$ intercostal space. A 1-cm segment of LCx before the first obtuse marginal branch was dissected free using both sharp and blunt dissections. Care was taken to minimize direct manipulation of the artery itself to avoid vessel spasm. An ameroid constrictor (2.75 mm, Research Instruments, Corvallis, Oreg.) was placed around LCx. The pericardium and the chest were closed in layers and the anesthesia reversed. The animals were kept for 6 weeks to allow time for gradual occlusion of the LCx artery by ameroid constrictors.

Transmyocardial Revascularization

At 6 weeks following the insertion of ameroid constrictors, animals were randomly assigned to 3 groups (n=5 each). Group I and II received 30 needle punctures whereas group III underwent sternotomy only. Group I and III will be harvested at I week post operatively and group II will be harvested at 4 weeks following TMR.

All TMR operations were performed through median sternotomy. Anesthesia and intubation were performed in the same fashion as the first operation. All animals received prophylactic intravenous xylocaine bolus (2 mg/kg) and were maintained on xylocaine infusion (1 mg/min) throughout the operation. Median sternotomies were performed and the hearts exposed by opening the pericardium and carefully dissecting away pericardial adhesions. Needle punctures were performed in an area measuring approximately 2×2 cm between the $1^{st}$ and $2^{nd}$ obtuse marginal arteries using 18 gauge hypodermic needles. Transmural penetration was confirmed by noting pulsatile bleeding of arterial blood through the needle. Bleeding was controlled with finger pressure or 4-0 prolene sutures, which also served as markers of puncture sites at the time of tissue harvest. Sternums were then closed with steel wires and the incisions closed in layers. Anesthesia was reversed and the animal allowed to recover.

Sample Harvest and Cryopreservation

At time of tissue harvesting, repeat sternotomies were performed through the same incision. Hearts were isolated by careful dissection of adhesions. Animals were euthanised with an overdose of pentobarbital and potassium chloride. The ascending aortas were cross-clamped and the hearts fixed in situ by injecting 1 liter of ice cold 4% paraformaldehyde through aortic root. Full thickness slices of myocardium from TMR treated area (or corresponding ischemic area in the control group) were removed and immediately immersed in 4% paraformaldehyde in PBS. These were kept at 4° C. for 12 hours. The specimens were then transferred into 15% sucrose in PBS and kept at 4° C. for 3 days. Afterwards, samples were embedded in OCT compound (Tissue-Tek, Sakura Finetek Inc., Torrance, Calif.) and snap frozen with liquid nitrogen and kept at −80° C.

All ameroid constrictors were retrieved from the heart and inspected to confirm vessel occlusion.

Sample Analysis

Immunohistochemistry

Cryostat sections of tissue samples were mounted on glass slides and immunostained with antisera to VEGF, bFGF, TGF-β (Santa Cruz Biotechnology Inc., Santa Cruz, Calif.), or factor VIII ligands (Sigma-Aldrich Canada Ltd., Oakville, Ontario) with a modified Avidin Biotin-Peroxidase method. Tissue sections were made permeable with Triton X-100, incubated in hydrogen peroxide to block endogenous peroxidase activity. They were then incubated first with normal goat serum for 30 minutes and followed with the primary antibody for 16 hours at 4° C. Afterwards, they were incubated with biotinylated immunoglobulin G and stained with an immunoperoxidase technique according to the manufacturer's instructions (Vectastain ABC Elite Kit: Vector Laboratories, Burlingame, Calif.).

Angiogenic Growth Factor Expression

Growth factor expression was quantified by measuring the area of tissue sections positively stained for VEGF, bFGF, or TGF-β in each high power field (BPF, 400×). Measurements were performed around TMR puncture sites, which were identified by the following criteria: 1) identifiable needle or laser tracks under low power view (LPV, 100×), 2) presence of inflammatory cells and granulation tissue, and 3) loss of normal myocyte appearance and homogeneity. Using the sampling method of 'systematic sampling with a random start', (Weibel E. Stereological Methods $1^{st}$ ed. Vol. 1 New York Academic Press, 1979) eight sampling sites from each tissue section were photographed with a still video camera and digitized into Tagged Image File Format (TIFF) files. Quantitative measurements of stained area were performed with an IBM compatible personal computer using Matrox Inspector 2.1 (Matrox Inc., Montreal, Canada). Total amount of growth factor expression for each animal was reported as mean area of positive stain ($mm^2$).

Vascular Density

TMR induced angiogenesis was quantified by measuring vascular density of VEGF and Factor VIII stained blood vessels per HPF around puncture sites. Positively stained vessels were defined as round structures with a central lumen, which was lined by a thin layer of endothelium stained positively for VEGF or factor VIII. Eight measurements were taken for each tissue section using the same sampling method. Results of angiogenesis for each animal were reported as mean number of vessels per HPF.

Statistical Analysis

Data were analyzed with student's t-test using SPSS 7.5.2 for Windows (SPSS Inc., Chicago, Ill.). A p-value of less than 0.05 was considered significant.

Results

Mortality

Two deaths occurred in Group M on post-operative day #2 following TMR. Autopsy showed severe pulmonary congestion and tissue edema with no evidence of myocardial infarction. The presumed cause of death was congestive heart failure.

Histology

All animals had complete occlusion of LCx at the time of sample harvesting. In TMR-treated specimens, the areas of transmural punctures were easily identified by the presence of numerous fibrous scars on the endocardium.

Under low-power light microscopic examinations, transmural puncture sites could be identified as central fibrous tracts surrounded by inflammatory changes. All channels were completely occluded by fibrosis. At 1 week following TMR (Group 1), the fibrous tracts consisted mainly of fibroblasts and collagen material with occasional small blood vessels. The surrounding area consisted of granulation tissue and damaged myocardium with infiltrating lymphocytes and macrophages. These were similar to the typical inflammatory changes during normal tissue healing process. Numerous small vascular structures were also found in the area of tissue inflammation. These vessels were morphologically indistinguishable from native myocardial capillaries except for their endothelium, which was positively stained for VEGF or factor VIII. Most of these vessels were smaller than 10 μm in diameter and were believed to be at various stages of angiogenic development.

Inflammatory changes related to needle punctures were limited to their immediate vicinity. Each puncture site was separated from others by normal looking myocardium indistinguishable from control specimen under light microscopy.

At 4 weeks after needle puncture (Group II), the transmural channels were completely replaced by fibrous scar tissue. There was significantly less inflammatory cellular infiltrate observed in the granulation tissue surrounding needle tracts. Compared to Group 1, fewer vessels with positively stained endothelium were found in Group II. However, the remaining vessels were more mature looking and had somewhat larger diameter.

Angiogenic Growth Factor Expression

Parallel comparison revealed that different angiogenic growth factors had distinct stain patterns. In samples taken 1 week following needle puncture (Group I), several cell types stained positively for VEGF, including endothelial cells, macrophages, fibroblasts, as well as myocytes. In general, positive stains were limited to areas adjacent to the puncture sites. Endothelium and macrophages gave the most intense stains but represented only a small portion of the total area as measured by computer assisted morphometry. On the other hand, myocytes and fibroblasts produced a more diffused staining pattern and represented most of the measurements for VEGF expression (0.47±0.03 $mm^2$ vs. 0.05±0.05 $mm^2$ $p<0.001$). Very little stains were present in areas away from puncture sites, and measurements from these areas were not significantly higher than the baseline.

At 4 weeks post TMR (Group II), there is less VEGF staining present in the endothelial cells and macrophages.

However, positive stain from myocytes; and fibroblasts persisted, and the overall level as measured by morphometric analysis was still significantly higher than that of control ($0.34\pm0.06$ mm$^2$ vs. $0.05\pm0.05$ mm$^2$ p=0.003).

Basic FGF stained much differently from that of VEGF. At 1 week post TMR (Group I), there was strong stain of fibroblasts along the needle tracts by anti-bFGF anti-sera ($0.67\pm0.14$ mm$^2$ vs. $0.03\pm0.03$ mm$^2$ p<0.001). Very little stain was found in other cell types. The level of bFGF stain dropped to baseline at 4 weeks (Group II, $0.06\pm0.02$ mm$^2$ vs. $0.03\pm0.03$ mm$^2$ p=0.135).

TGF-$\beta$ stain followed a similar pattern as that of VEGF at 1 week post TMR (Group 1), i.e. endothelial cells, macrophages, myocytes, and fibroblasts. Again, most of the morphometric measurement was from myocytes and fibroblasts, which gave a more diffuse stain pattern ($1.40\pm0.18$ mm$^2$ vs. $0.09\pm0.06$ mm$^2$ p<0.001). At 4 weeks (Group II), the level of stain had decreased considerably but was still significantly higher than that of the baseline ($0.28\pm0.09$ mm$^2$ vs. $0.09\pm0.06$ mm$^2$ p=0.042).

Angiogenesis

At 1 week following needle puncture (Group I), there was a significant increase in the number of vascular structures in the vicinity of needle punctures. This increase in vascular density was found by both VEGF staining ($8.1\pm0.6$ vs. $1.1\pm0.5$ p<0.001) and Factor VIII staining ($5.1\pm2.7$ vs. $0.4\pm0.3$ p=0.018). These vessels were mostly between 2–10 $\mu$m in diameter and were believed to be at various stages of angiogenic development.

The number of VEGF stained vessels dropped to baseline at 4 weeks ($1.9\pm0.5$ vs. $1.1\pm0.5$ p=0.107), while the number of Factor VIII stained vessels was lower but still significantly higher than that of the control ($2.3\pm0.4$ vs. $0.4\pm0.3$ p=0.004).

In the past two decades, all clinical studies of TMR for the treatment of ischemic angina have been in the form of laser TMR (TMLR). This is not surprising, since laser industry has been instrumental in providing technical and financial support for this procedure from the beginning. Although there is no evidence supporting the benefit of laser, TMLR remains to be the only procedure available in clinical practice. Without a clear understanding of its mechanism, this situation will likely remain unchanged despite the technical complexity and significant cost associated with laser TMR.

Debates over the basic mechanism of TMR have a history almost as long as that of the procedure itself. The initial 'open-channel' hypothesis based on a reptilian style transmural perfusion is no longer supported by the currently available research data. Not only there is a lack of evidence indicating the existence of patent channels beyond immediate post-op period, the potential amount of blood flow through these channels is also insignificant due to physiological limitations. More recently, several other hypotheses have been proposed in an effort to explain the apparent effectiveness of TMR in reducing angina symptoms, among these, is angiogenesis.

TMR induced angiogenesis is based on the observation that significant inflammatory reaction is consistently found in the vicinity of myocardial punctures. It is well known that angiogenesis and neovascularization play a central role during the initial phases of wound healing. This angiogenic response is stimulated by various growth factors released as a result of tissue injury and inflammatory cellular infiltration. The end result is seen as increased vascular density in the injured area. Central to this angiogenic hypothesis is that the release of angiogenic growth factors is a nonspecific response to tissue injury, which can be created by a variety of methods. Although laser was initially used to improve long-term channel patency, perhaps its true value is simply being a glamorous way to incite myocardial injury. In fact, a recent study of TMR by radio frequency ablation (RF-TMR) in a chronic ischemic porcine model also showed increased angiogenesis. Furthermore, simple needle punctures of myocardium have also been shown to induce an angiogenic response in an acute ischemic rat model. This is especially interesting, because transmyocardial needle acupuncture was the only TMMR method that has seen clinical applications. More recently, it has been shown that at 1 week post TMR, treatments with both needle and $CO_2$ laser punctures resulted in similar increase in the expression of VEGF and tissue vascular density.

At 1 week following TMMR procedure, there was an intense inflammatory reaction surrounding myocardial puncture sites, which is characteristic of a wound healing process. The intensity of tissue inflammation markedly reduced at 4 weeks post-op as the healing process moves from inflammatory towards the proliferating phase. As expected, different growth factors had distinct stain patterns, which is a reflection of their intrinsic protein syntheses and ligand bindings. All three growth factors had significantly elevated level of expression at 1 week. At 4 weeks, the levels of VEGF and TGF-$\beta$ decreased significantly as a result of diminished inflammatory cellular infiltrates and less stain of myocytes and fibroblasts. However, their levels remained elevated when compared to those of control. On the other hand, bFGF stain was mainly limited to the fibroblasts along needle puncture sites, and its level returned to baseline with maturing of the scar tissue. Persistent expression of VEGF and TGF-$\beta$ at 4 weeks post TMR was also seen by others using $CO_2$ and Holmium-YAG laser.

Vascular endothelial growth factor is a potent direct stimulant of neovascularization and vessel proliferation with receptors on the endothelial cells. Significantly higher number of developing vessels with VEGF stained endothelium were found at 1 week. It is postulated that these were newly formed vessels stimulated by locally secreted VEGF. When sections from the 4-week group were analyzed, the number of VEGF stained vessels had decreased to that of the baseline. However, this was mostly due to decreased VEGF binding to its endothelial receptors rather than disappearance of newly formed vessels. Staining with Factor VIII confirmed that vascular density was reduced but still significantly higher than that of controls.

Needle TMMR in accordance with the invention is effective in stimulating intrinsic expression of several different angiogenic growth factors, and these findings were fundamentally indistinguishable from other studies of TMR using laser devices.

EXAMPLE 2

A study of multiple punctures of the ischemic myocardium was carried out to demonstrate the safety of the techniques.

In 20 patients undergoing conventional coronary artery surgery, 25 to 30 punctures were formed in accordance with the invention, in an area of the heart which could not be revascularized by conventional means. There was no evidence of catastrophic bleeding in the patients. One patient dies as a result of myocardial infarction in a region of the heart remote from the puncture area, the remaining 19 patients did well and had no residual angina.

In addition to the revascularization achieved by the punctures produced by the device of the invention in the method of the invention, revascularization of an ischemic myocardium may be achieved by delivering angiogenic growth factors such as vascular endothial growth factors (VEGF), fibroblastic growth factors (GFG) and transforming growth factors (TGF). Furthermore, the device may be employed to deliver angiogenic precursor cells (stem cells) of adult (stromal) or fetal (embryonical) types.

The device and method may be employed to treat ischemic myocardium or to treat a failing myocardium through the ability to cause angiogenesis, and the ability to deliver myogenic factors and myoblast precursor cells which can be, for example, fetal or adult type (skeletal myoblast or satellite cells).

We claim:

1. A method of transthoracic angiogenesis or myogenesis of a myocardium comprising:

puncturing a myocardium from epicardium to endocardium, simultaneously, at a plurality of spaced apart sites, with a plurality of needles, and simultaneously withdrawing the plurality of needles from the punctured myocardium.

2. A method according to claim 1, for revascularizing an ischemic myocardium, wherein the punctured myocardium is an ischemic myocardium.

3. A method according to claim 1, wherein said plurality of needles is supported in spaced apart relationship by a support member, and comprising:

concealing said needles with a shield member, introducing said support member with the concealed needles into close proximity with the ischemic myocardium, exposing said needles for the step of puncturing, and reconcealing said needles with said shield member after the step of puncturing.

4. A method according to claim 1, including injecting at least one agent into the punctures in the myocardium through said needles.

5. A method according to claim 4, wherein said at least one agent comprises a growth factor.

6. A method according to claim 5, wherein said growth factor is an angiogenic growth factor selected from vascular endothial growth factors, fibroblastic growth factors and transforming growth factors.

7. A method according to claim 4, wherein said agent comprises angiogenic precursor cells.

8. A method according to claim 1, wherein said transthoracic method comprises a step of providing access to the myocardium by left thoractomy incision, thoracoscopically or by sternotomy.

9. A method according to claim 1, wherein said plurality of needles is supported in spaced apart relationship by a support member, said needles extruding from a support face of said support member, said plurality being 5 to 15 and said needles having a maximum diameter of at least 1.25 mm and a length effective to provide a puncture depth of 6 to 20 mm.

10. A method according to claim 9, wherein said support face is substantially flat and said needles are in spaced apart parallel relationship extending perpendicularly of said support face, said needles having a maximum diameter of 1.25–1.8 mm and adjacent needles being spaced apart with their central axes 2 to 4 mm apart.

11. A device for transthoracic angiogenesis or myogenesis of a myocardium comprising:

a support member dimensioned for insertion into proximity with a myocardium, and a plurality of needles supported by said support member in spaced apart relationship, said needles being effective to puncture the myocardium from epicardium to endocardium;

wherein said support member has a support face and said needles extend from said support face, said plurality being 5 to 15 and said needles having a maximum diameter of at least 0.125 mm and a length effective to provide a puncture depth of 6 to 20 mm.

12. A device according to claim 11, wherein said support face is substantially flat and said needles are in spaced apart parallel relationship extending perpendicularly of said support face, said needles having a maximum diameter of 1.25–1.8 mm and adjacent needles being spaced apart with their central axes 2 to 4 mm apart.

13. A device for transthoracic angiogenesis or myogenesis of a myocardium comprising:

a support member dimensioned for insertion into proximity with a myocardium, and a plurality of needles supported by said support member in spaced apart relationship, said needles being effective to puncture the myocardium from epicardium to endocardium;

further comprising a shield member, at least one of said support member and said shield member being displaceable relative to the other from a first position in which said needles are concealed, in a non-puncturing configuration, by said shield member, to a second position in which said needles are exposed for puncturing, and means to displace said at least one said member relative to the other between said first and second positions as required.

14. A device for transthoracic angiogenesis or myogenesis of a myocardium comprising:

a support member dimensioned for insertion into proximity with a myocardium, and a plurality of needles supported by said support member in spaced apart relationship, said needles being effective to puncture the myocardium from epicardium to endocardium;

wherein at least some of said needles have a conduit therethrough terminating at an outlet of the needle point, the conduits having an inlet communicating with a supply zone in the interior of said support member, for supply of an exogeneous angiogenic or myogenic factor to the myocardium through said conduits.

15. A device according to claim 13, wherein at least some of said needles have a conduit therethrough terminating at an outlet of the needle point, the conduits having an inlet communicating with a supply zone in the interior of said support member, for supply of an exogeneous angiogenic or myogenic factor to the myocardium through said conduits.

16. A device according to claim 13, wherein said support member has a support face and said needles extend from said support face, said plurality being 5 to 15 and said needles having a maximum diameter of at least 1.25 mm and a length effective to provide a puncture depth of 6 to 20 mm.

17. A device according to claim 14, wherein said support member has a support face and said needles extend from said support face, said plurality being 5 to 15 and said needles having a maximum diameter of at least 1.25 mm and a length effective to provide a puncture depth of 6 to 20 mm.

18. A device according to claim 15, wherein said support member has a support face and said needles extend from said support face, said plurality being 5 to 15 and said needles having a maximum diameter of at least 1.25 mm and a length effective to provide a puncture depth of 6 to 20 mm.

* * * * *